US00PP15019P2

(12) United States Plant Patent
Zary

(10) Patent No.: US PP15,019 P2
(45) Date of Patent: Jul. 13, 2004

(54) MINIATURE ROSE PLANT NAMED 'JACREPOR'

(50) Latin Name: *Rosa hybrida*
Varietal Denomination: JACrepor

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,572

(22) Filed: Nov. 19, 2002

(51) Int. Cl.[7] ..... A01H 5/00
(52) U.S. Cl. ..... Plt./122
(58) Field of Search ..... Plt./122, 116, 129

*Primary Examiner*—Anne Marie Grunberg
*Assistant Examiner*—June Hwu
(74) *Attorney, Agent, or Firm*—Klarquist Sparkman LLP

(57) ABSTRACT

Miniature rose plant having high petal count of flowers of stable, red color; long shelf life as a pot rose; absence of pollen; and its ability to grow well on its own roots.

1 Drawing Sheet

Genus and species: *Rosa hybrida*.
Variety denomination: 'JACrepor'.

SUMMARY OF THE INVENTION

The present invention relates to a new and distinct variety of miniature rose plant named 'JACrepor' which was originated by me by crossing the variety 'KORstoffein', U.S. Plant Pat. No. 11,242, with an unnamed seedling.

BACKGROUND OF THE INVENTION

The primary objective of this breeding was to produce a new rose variety having the high petal count, hard petals, and long shelf life of the female parent with the compact plant and red flower color of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. High petal count;
2. Stable red color;
3. Very long shelf life as pot rose;
4. Absence of pollen;
5. Ability to grow well on its own roots; and
6. Highly adaptability to grow in 10 cm pots.

Asexual reproduction of this new variety by rooting cuttings, as performed at Somis, Calif., shows that the foregoing and all other characteristics and distinctions come true to form and are established and transmitted through succeeding propagations.

Comparison with Parents

The female parent 'KORstoffein' is a light pink pot rose with 2.5 cm flowers, the plant having a shelf life of about twenty-one days. The male parent has red, 6.5 cm flowers, the plant having a shelf life of about seven days.

Comparison with Similar Variety

'KORhomapo' (U.S. Plant Pat. No. 11,148) is a similar variety but possess dark red flowers of larger size but fewer petals and also bears longer leaves.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'KORstoffein' (U.S. Plant Pat. No. 11,242).
*Pollen parent.*—Unnamed seedling. (Unpatented).

FLOWER

Observations made from plants beginning at two years of age grown in a greenhouse environment at Somis, Calif., June, 2000 to June, 2001.

Blooming habit: Continuous.
Bud:
*Size.*—About 20 mm long when the petals start to unfurl.
*Form.*—The bud form is long.
*Color.*—When sepals first divide, bud color is Red Group 53A. When half blown, the upper sides of the petals are Red Group 53A; and the lower sides of the petals are Red-Purple Group 60B.
*Sepals.*—Color: Upper surface: Green Group 138B. Lower surface: Green Group 137B. Length: 23–26 mm. Width: 5–7 mm. Shape: Subulate. Apex Shape: Caudate. Surface texture: Upper: Covered in fine hairs. Lower: Smooth with a few fine hairs. There are three heavily appendaged sepals. There are two unappendaged sepals with hairy edges.

*Receptacle.*—Color: Yellow-Green Group 144A. Shape: Funnel. Size: Small, about 6 mm long×6 mm wide. Surface: Smooth.

*Peduncle.*—Length: Long, averaging about 55–65 mm. Surface: Prickly, glandular. Color: Yellow-Green Group 144A. Strength: Stiff, erect.

Bloom:

*Size.*—Large, for a miniature. Average open size is 55–60 mm.

*Borne.*—Singly.

*Stems.*—Strength: Strong. Average length is about 18–22 cm.

*Form.*—When first open: High centered. Permanence: Flattens, all petals curl back in quill fashion.

*Petalage.*—Number of petals under normal conditions: 60–70.

*Color.*—The upper sides of the petals are Red Group 53A. The reverse sides of the petals are Red-Purple Group 60B. The base of each petal has on the upper surface is Yellow Group 4C; the lower surface is Yellow Group 4D. The major color on the upper side is Red Group 53A.

*Variegations.*—Occasionally on guard petals a stripe of Green Group 138C.

*Discoloration.*—The general tonality at the end of the first day: No change. At the end of the third day: No change. By day 15 or 16, there is a general bluing of the petals to Red-Purple Group 60B and then falling by day 18.

*Fragrance.*—None.

Petals:

*Texture.*—Leathery.

*Margin.*—Entire.

*Shape.*—Obovate.

*Apex shape.*—Mucronate.

*Base shape.*—Obtuse.

*Size.*—Length: 2 cm; width 4 cm.

*Form.*—Tips slightly recurved, edges slightly quilled.

*Arrangement.*—Imbricated.

*Petaloids.*—Number: 10–15 Color: Red group 53A. Size: Width: 1 mm. Length: 3 mm. Surface Texture: Glabrous.

*Persistence.*—Petals drop off cleanly before drying.

*Lastingness.*—On the plant: Long (about 16–18 days). As a cut flower: Long (about 18–20 days).

Reproductive parts:

*Stamens.*—Number: 15–20. Length: 6–9 mm. Anthers: Length: 1 mm. Color: Yellow-Orange Group 22B. Arrangement: Regular around styles, mixed with petaloids. Filaments: Color: Yellow-Orange Group 18D. Length: 5–8 mm. Pollen: Unknown, will not dehiss from pollen stack (sterile).

*Pistils.*—Number: 40–45. Styles: Color: Yellow Group 2D. Length: 3–4 mm. Stigmas: Color: Yellow-White Group 158D. Length: 1 mm.

*Hips.*—None observed.

PLANT

*Form.*—Bush.

*Growth.*—Vigorous, upright, branching and compact.

*Mature plant.*—Height: 30 cm. Width: 20 cm on a plant 16 weeks old grown in a 10 cm pot.

Foliage: Number of leaflets on normal mid-stem leaves: 5.

*Size.*—Medium (for a miniature) (8–10 cm long×6.5–7 cm wide).

*Quantity.*—Normal.

*Color.*—New foliage: Upper side: Green Group 137A with anthrocyanin pigmentation on leaf margin edges (Greyed-Purple Group 183B). Lower side: Greyed-Purple Group 183C quickly turning green. Old foliage: Upper side: Between Green Group 137A and 139A. Lower side: Green Group 138B.

Leaflets:

*Size.*—Length: 16–18 mm. Width: 10–11 nm.

*Shape.*—Ovate.

*Base shape.*—Obtuse.

*Apex shape.*—Acute.

*Texture.*—Smooth.

*Edge.*—Serrated.

*Serrations.*—Single, small.

*Petiole rachis.*—Color: Yellow-Green Group 145B. Underside: With prickles and occasional glands.

*Stipules.*—Short (about 5 mm×3 mm); serrated.

*Disease resistance.*—Susceptible to mildew and black-spot under normal growing conditions in a greenhouse. Rust not observed.

*Pest resistance.*—Not tested.

*Vein color.*—Yellow Green-Grey Group 145B.

*Venation pattern.*—Reticulate.

Wood:

*New wood.*—Color: Yellow-Green Group 146B. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Long, straight.

*Color when young.*—Greyed-Red Group 179D.

*Color when mature.*—Greyed-Orane Group 165D.

Small prickles:

*Quantity.*—On main stalks: None. On laterals: None.

Winter hardiness: Hardy to Zone 5.

I claim:

1. A new and distinct variety of rose plant of the miniature class, substantially as herein shown and described, characterized particularly by high petal count of flowers of stable, red color; long shelf life as a pot rose; absence of pollen; and its ability to grow well on its own roots.

* * * * *

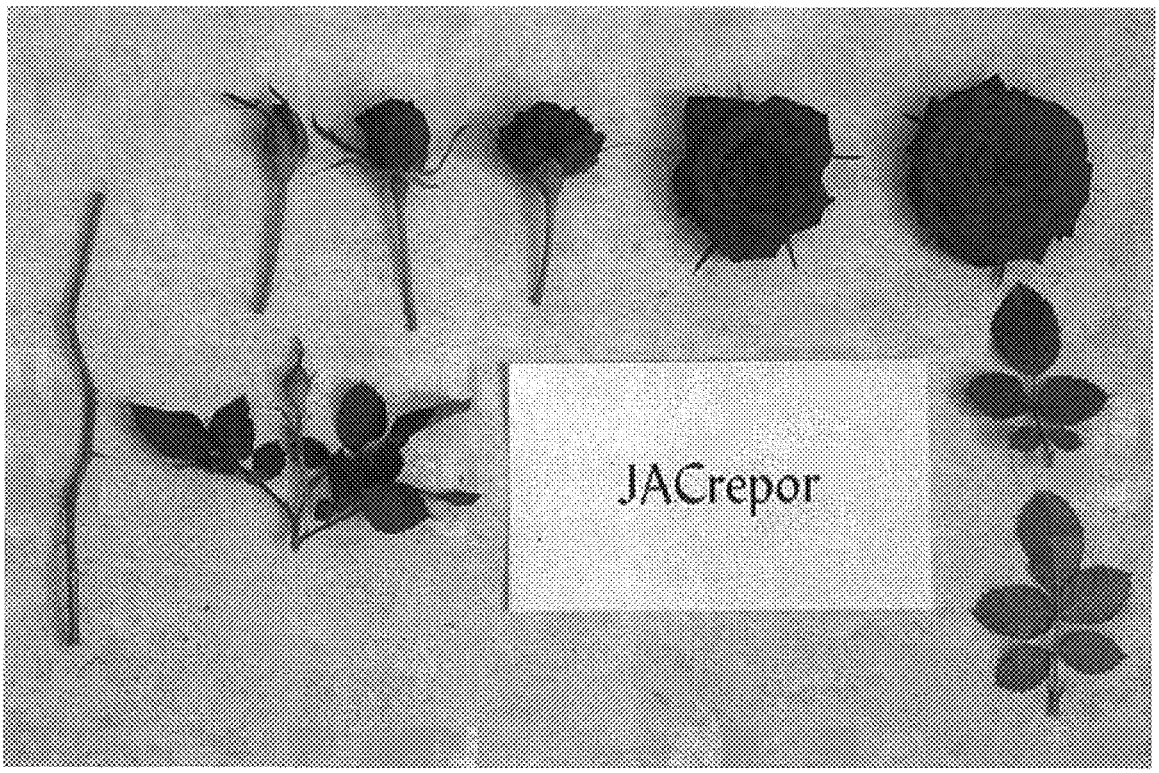
JACrepor